United States Patent [19]
Burkhart

[11] Patent Number: 5,746,752
[45] Date of Patent: May 5, 1998

[54] DOUBLE-DIAMETER KNOT PUSHER

[75] Inventor: Stephen S. Burkhart, San Antonio, Tex.

[73] Assignee: Arthrex, Inc., Naples, Fla.

[21] Appl. No.: 745,189

[22] Filed: Nov. 7, 1996

Related U.S. Application Data

[60] Provisional application No. 60/006,390 Nov. 8, 1995.

[51] Int. Cl.⁶ .................................................. A61B 17/04
[52] U.S. Cl. ........................ 606/139; 606/139; 606/144
[58] Field of Search ............................ 606/139, 148, 606/144; 112/169; 289/17

[56] References Cited

U.S. PATENT DOCUMENTS

| | | | |
|---|---|---|---|
| 4,796,626 | 1/1989 | De Vries | 606/148 |
| 5,059,201 | 10/1991 | Asnis | 606/139 |
| 5,084,058 | 1/1992 | Li | 606/139 |
| 5,100,415 | 3/1992 | Hayhurst | 606/139 |
| 5,192,287 | 3/1993 | Fournier et al. | 606/148 |
| 5,217,471 | 6/1993 | Burkhart | 606/148 |
| 5,312,423 | 5/1994 | Rosenbluth et al. | 606/148 |
| 5,591,177 | 1/1997 | Lehrer | 606/139 |
| 5,643,293 | 7/1997 | Kogasaka et al. | 606/139 |

*Primary Examiner*—Gary Jackson
*Attorney, Agent, or Firm*—Ostrolenk, Faber, Gerb & Soffen, LLP

[57] ABSTRACT

A disposable, double-diameter knot pusher for use in arthroscopic surgery. The knot pusher is formed of two telescoped tubes, specifically, an inner, smaller diameter pusher tube slidably disposed within an outer, larger diameter pusher tube. The first knot is thrown around the suture post limb, and is pushed along the post limb with the inner tube. The inner tube holds the first knot in place, while the second knot is thrown around the inner tube and pushed into place with the outer tube. A suture passer is used to draw a post section of suture through the inner tube to begin the knot-tying process.

20 Claims, 5 Drawing Sheets

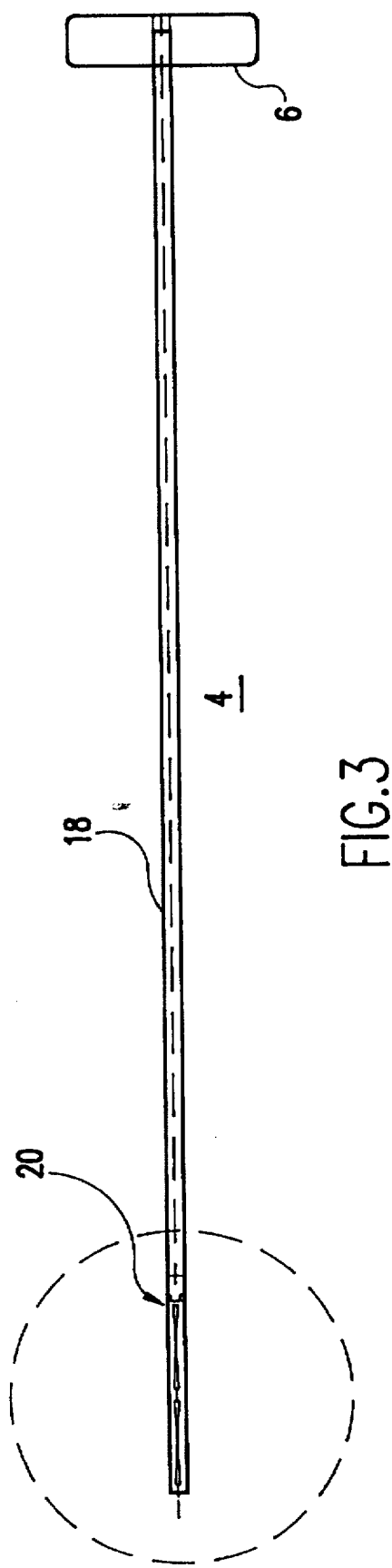
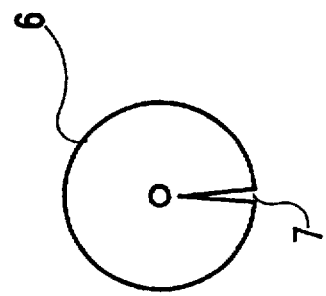
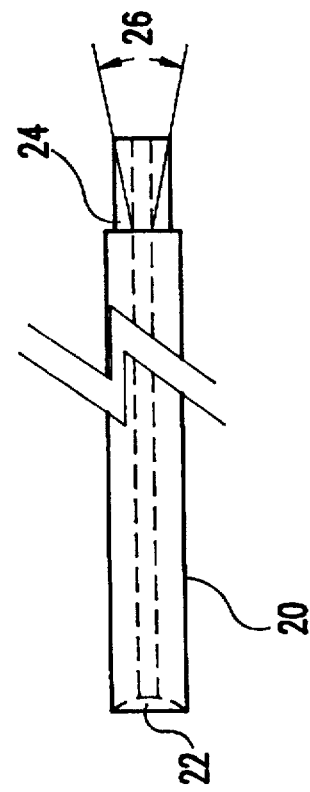
FIG.3
FIG.5
FIG.4

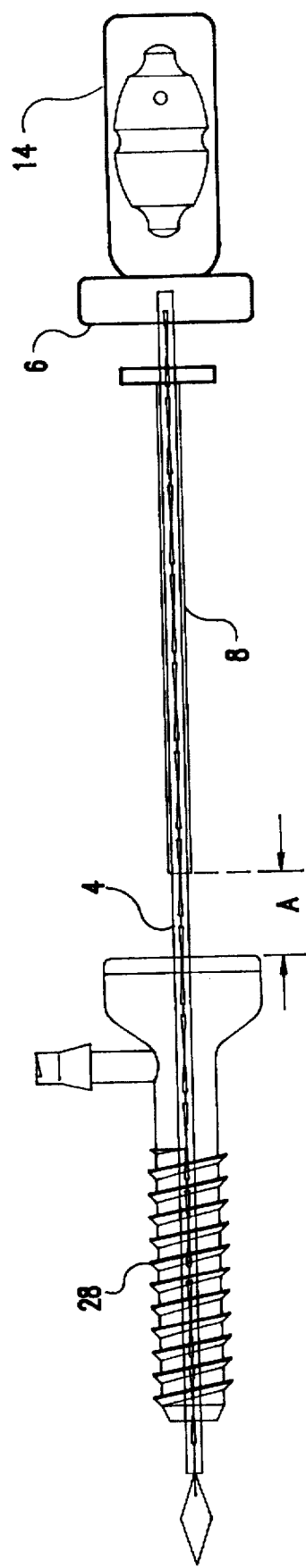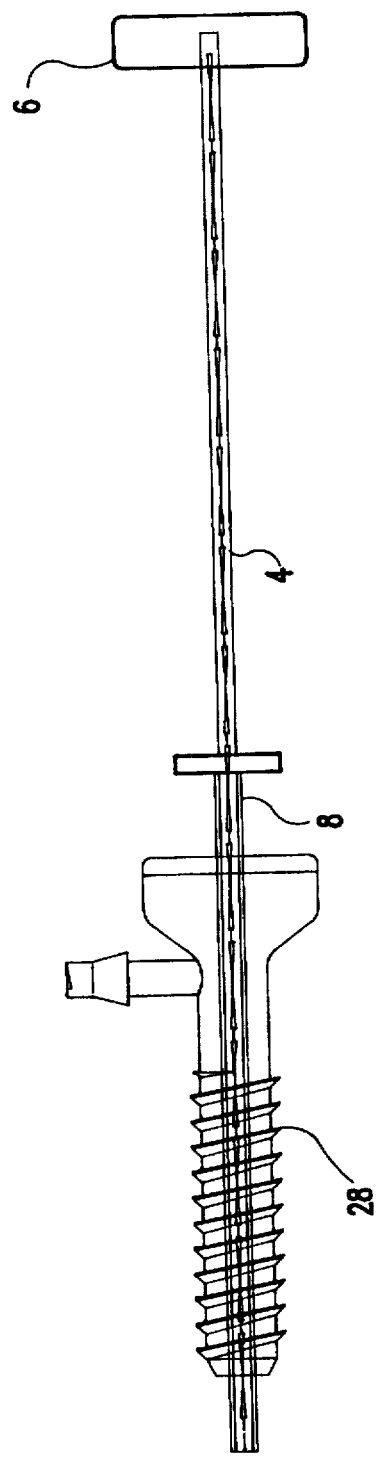
FIG.6
FIG.7

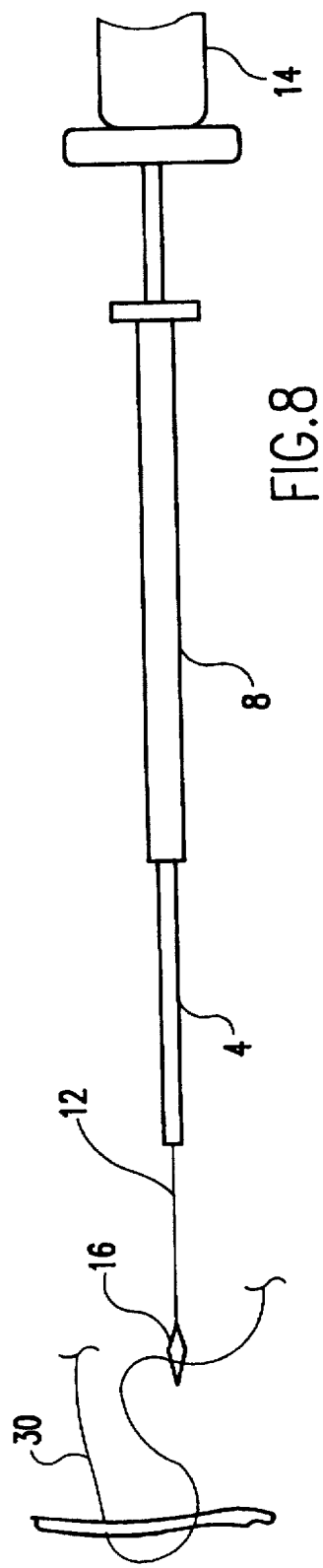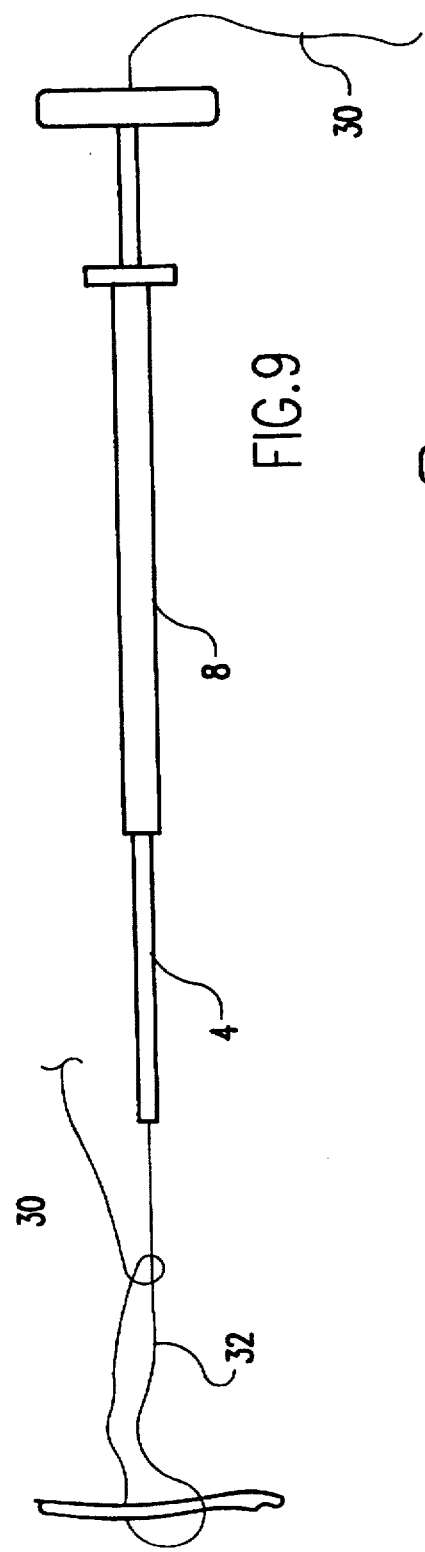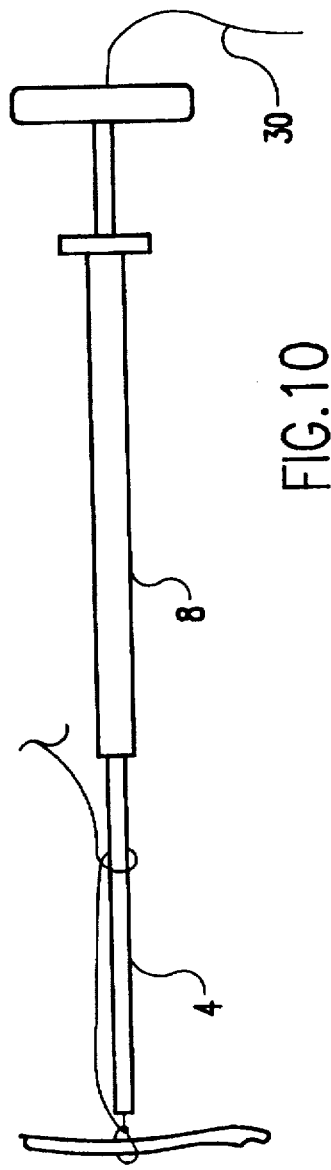

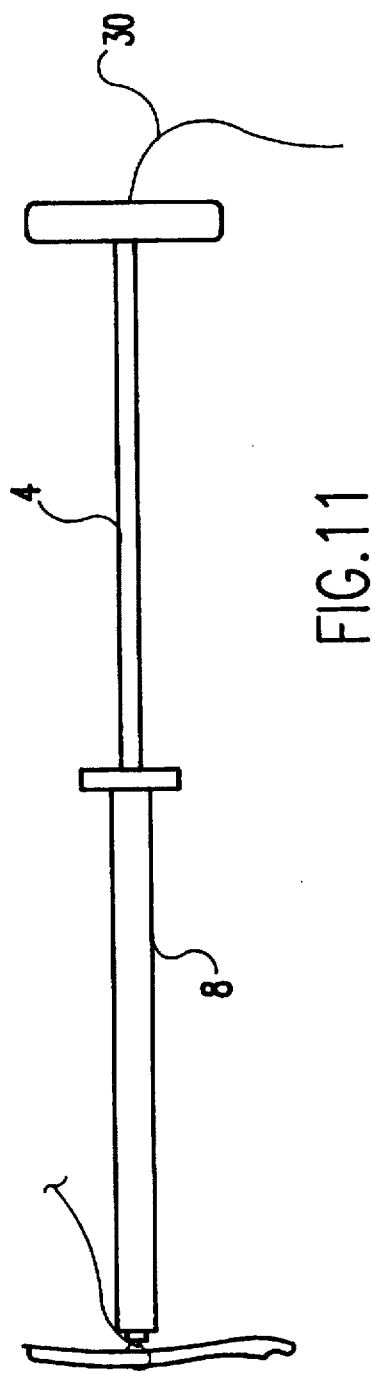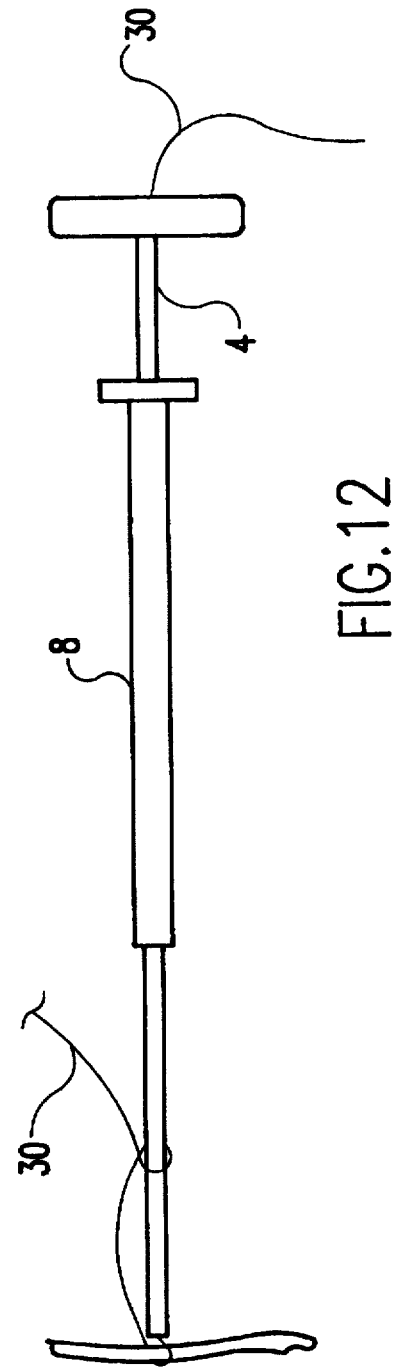

DOUBLE-DIAMETER KNOT PUSHER

This application claims the benefit of U.S. Provisional Application Ser. No. 60/006,390, filed Nov. 8, 1995, the disclosure of which is incorporated herein by reference.

BACKGROUND OF THE INVENTION

1. Field of the Invention

The invention relates to knot pushers used in surgery, and more specifically, to a disposable, double-diameter knot pusher used in arthroscopic surgery to tie knots in suture at a remote sight inside the body.

2. Description of the Related Art

Various styles of knot pushers have been developed to address the need to tie knots in suture during surgical procedures, particularly arthroscopic procedures. The knot pushers are used, for example, to push consecutive half hitches formed around a limb of suture referred to as the post.

Generally, a half hitch is started as a loop formed outside the body. The loop is then pushed through a portal in the skin to a remote site within the body. The knot pusher advances the loop distally along the post, so as to gather and secure soft tissue, for example, at the remote site of repair within the patient.

One of the problems with arthroscopic knot tying until now has been the inability to tie a tight knot in a predictable manner. Oftentimes, the first half hitch relaxes and loosens before the second half hitch can be brought into position to hold it. Sometimes, when gathering together loose soft tissues, for example, the knot can be kept tight. The problem of loosening becomes worse, however, when tying a knot against harder surfaces, such as bone, for example. The first loop invariably loosens before it can be secured by the second half hitch.

Therefore, the need exists for a surgical device that ties a tight knot predictably and simply, by holding the first throw of a suture knot while the second throw is brought into place over the first throw. The device should be disposable, and provided in sterile condition for single-use application.

SUMMARY OF THE INVENTION

The present invention overcomes the problems associated with the prior art by providing a disposable, sliding knot pusher. The knot pusher includes an elongated inner pusher tube slidably disposed within a shorter, elongated outer pusher tube. The assembled tubes fit within a cannula providing arthroscopic access to a remote site within a body undergoing surgery. Although cylindrical tubes are described and illustrated herein, other tube shapes, such as square or oblong, are encompassed by the present invention.

Suture knots are tied with the knot pusher by threading a post limb of suture through the lumen of the inner tube. A small wire loop disposed on a thin rod, for example, that fits within the inner tube, can be used for threading. A first half-hitch loop is thrown around the post suture, and the inner tube is advanced distally along the post suture. The distal end of the inner tube contacts the half-hitch and pushes the loop into place to tighten the first half hitch. The inner tube is then held against the first half hitch, keeping the knot held tight in a fashion similar to the way a half hitch is held with one's finger.

Alternatively, the first loop can be thrown around the inner tube itself, through which the post limb of suture has been threaded. Advantageously, the distal end of the inner tube can be used to hold tissue in place while the first loop is in place around the inner tube. The first loop is then pushed with the distal end of the outer tube advancing distally along the outside of the inner tube. As the first loop is tightened, the knot is slipped over the distal end of the inner tube. The inner tube then can hold the first throw firmly, as against tissue, for example.

According to this alternative method, the suture slides along the smooth outer surface of the inner tube, instead of along the post suture. Accordingly, this alternative method avoids abrasions that can be caused by suture rubbing against suture, which can be of concern particularly when using braided suture.

Once the first loop is in place, as formed by either method, a second loop can be thrown around the inner tube, between the first half hitch and the outer tube. The outer tube is advanced to push the second half hitch loop distally toward the end of the inner tube. The surgeon can then lock the two half hitches by tightening the second loop into a knot.

The steps can be repeated to form consecutive half hitches. The present invention provides a simple apparatus for predictably tying the series of half hitch knots by keeping the previous half hitch tight until the subsequent half hitch is advanced distally to lock the knot.

The knot pusher has application in arthroscopic procedures, including but not limited to arthroscopic rotator cuff repair, Bankhart shoulder repair, meniscal repair, and any orthopaedic procedure that requires tying a knot through soft tissue or bone tunnels, for example, or in conjunction with fixation devices, such as suture anchors.

In addition, the knot pusher has widespread application to other general surgical and specialty procedures that require suturing or knot tying at a remote site, such as inside the body. For example, the knot pusher of the present invention can be used in mini-open repairs, where knot visibility or finger access can be limited.

Other features and advantages of the present invention will become apparent from the following description of the invention which refers to the accompanying drawings.

BRIEF DESCRIPTION OF THE DRAWINGS

FIG. 3 is a detail view showing an inner tube according to a preferred embodiment of the present invention.

FIG. 4 is a detail sectional view showing the tip of the inner tube of FIG. 3.

FIG. 5 is an end view of the handle of the inner tube showing the suture retaining notch.

FIG. 6 is a side view of a knot pusher into which a suture passing loop has been inserted, and the assembly has been inserted through a cannula, according to a preferred embodiment of the present invention.

FIG. 7 is a side view of a knot pusher inserted through a cannula, the outer pusher tube having been advanced into the cannula, according to a preferred embodiment of the present invention.

FIG. 8 is a schematic side view of a knot pusher illustrating a first step in a method of suture knot tying according to a preferred embodiment of the present invention.

FIG. 9 is a schematic side view of a knot pusher illustrating a second step in a method of suture knot tying according to a preferred embodiment of the present invention.

FIG. 10 is a schematic side view of a knot pusher illustrating further steps in a method of suture knot tying according to a preferred embodiment of the present invention.

FIG. 11 is a schematic side view of a knot pusher illustrating a final step in a method of suture knot tying according to a preferred embodiment of the present invention.

FIG. 12 is a schematic side view of a knot pusher illustrating a step in an alternative method of suture knot tying according to a preferred embodiment of the present invention.

DETAILED DESCRIPTION OF THE INVENTION

Figure 1:
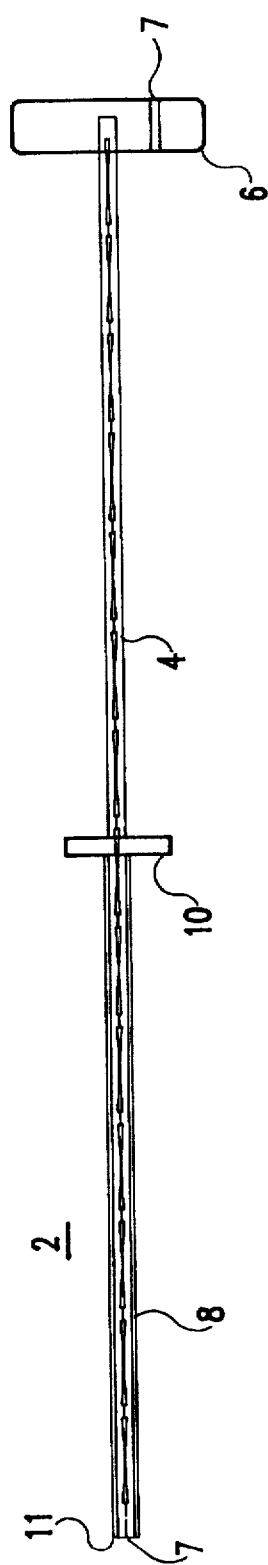
FIG. 1 is a side view of a knot pusher according to a preferred embodiment of the present invention.

Referring first to FIG. 1, a side view of a knot pusher 2 according to a preferred embodiment of the present invention is shown. Knot pusher 2 includes an inner tube 4, slidably disposed within outer tube 8.

Inner tube 2 is a small-diameter, thin-walled tube, preferably machined from stainless steel, having a distal end and a proximal end. A cannulated handle 6 is disposed on the proximal end of the tube. Cannulated handle 6 preferably is a separate piece secured over the proximal end of inner tube 4. Handle 6 includes a suture retaining notch 7, shown more clearly in FIG. 5. Handle 6 preferably is formed of a plastic material, such as molded polycarbonate. The distal end of inner tube 2 forms a face 9 described in further detail below.

Outer tube 8 also is a thin-walled tube, having a larger diameter than inner tube 6. Outer tube 8 preferably is formed of a plastic material, most preferably molded polycarbonate. Outer tube 8 fits slidably over inner tube 4, so that suture can be advanced distally along the outside of inner tube 4, using a face 11 formed at the distal end of outer tube 8.

The fit between the inner tube and the outer tube, especially at the distal end of outer tube 8, preferably is sufficiently tight to prevent suture from getting snagged in the space between the two tubes, without impeding the smooth sliding operation of the device. Accordingly, the diameter of the outer surface of inner tube 6 is only slightly less than the diameter of the lumen of outer tube 8.

A handle 10 is provided on the proximal end of outer tube 8 to assist in manipulating knot pusher 2. The opening through handle 10 can be chamfered to assist in insertion of inner tube 6, for example.

In FIG. 1, outer tube 8 is shown positioned toward the distal end of inner tube 4 such that the distal ends of the inner and outer tubes are substantially aligned. The assembled knot pusher, preferably includes a suture passer, described below, and preferably is provided as a sterile, single-use instrument, and need not be autoclavable.

Figure 2:
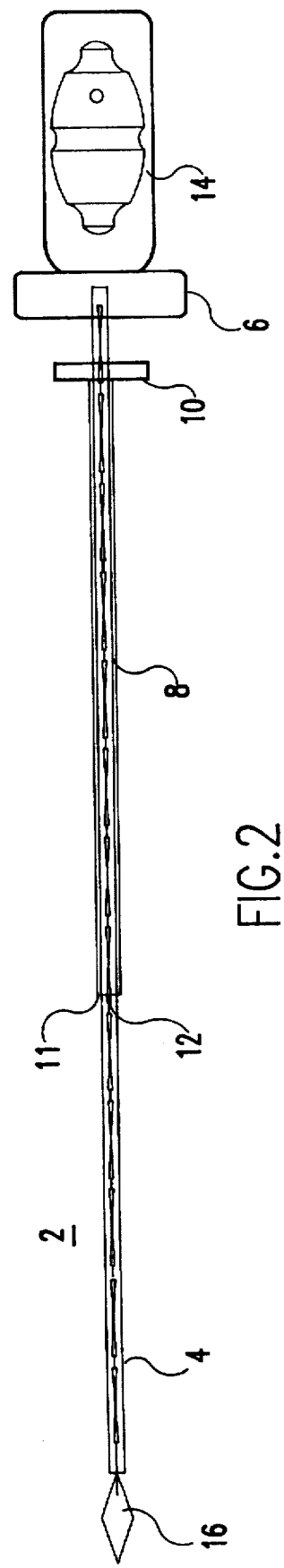
FIG. 2 is a side view of a knot pusher into which a suture passing loop has been inserted according to a preferred embodiment of the present invention.

Referring to FIG. 2, a suture passer 12 is shown inserted within knot pusher 2. Suture passer 12 includes a handle 14 that extends beyond the proximal end of inner tube 4, and a suture-capturing loop 16 secured to the distal end of the handle 14.

In FIG. 2, outer tube 8 has been positioned toward the proximal end of inner tube 4 such that the handles of the inner and outer tubes are substantially aligned.

Referring to FIGS. 3 and 4, further details of the knot pusher according to an alternative embodiment of the present invention are shown. FIG. 3 shows inner tube 4 with outer tube 8 removed. Inner tube 4 includes a body 18 having a tip 20 provided on the distal end thereof. Tip 20 is a separate, cannulated piece and has a radiused cup 22 on its distal end. Cup 22 facilitates controlling the suture knot when pushing the knot loop along the post limb of suture. In addition, the edges formed around the cup assist in positioning and holding tissue with the tip. The proximal end of tip 20 has a small-diameter section 24 received within a recess in the distal end of body 18 of inner tube 4. The lumen of tip 20 flares out at an angle 26 of approximately 20° to eliminate any edges that could prevent suture passer 12 from sliding smoothly within inner tube 4.

According to another alternative, and as a practical matter, the distal end of the tip can have a flat face, as shown in FIG. 1. The size of the flat face, according to this embodiment, is determined by the thickness of the outer tube. The thickness of the flat face generally is greater than or equal to the thickness of a strand of suture to be tied around the inner tube, but in any event is sufficient to engage and advance a piece of suture along the inner tube. Similarly, the thickness of the inner tube generally will be greater than or equal to the thickness of a strand of suture to be tied using the present invention, but in any event is sufficient to engage and advance a piece of suture along the post suture.

Referring to FIGS. 6 and 7, the knot pusher 2 is shown received within a cannula 28. In FIG. 6, inner tube 4 is inserted within cannula 28. As described in further detail below, in this position inner tube 4 will have pushed a first knot distally along a post limb of suture, through cannula 28 to a remote site in the body. Alternatively, inner tube 4 can be holding tissue at the remote repair site, awaiting a first half-hitch to be thrown around the inner tube and advanced to the remote site.

In the position shown in FIG. 6, inner tube 4 can hold the first knot tight and in place, once the knot has been formed and advanced to the end of the tube. Outer tube 8 is positioned toward the proximal end of inner tube 4, ready to push a half-hitch loop formed around the inner tube distally through cannula 28 to the remote sight. The relative lengths of inner tube 4 and outer tube 8 are selected to leave between the proximal end of cannula 28 and the distal end of outer tube 8 a distance A sufficient to throw a half-hitch loop around inner tube 4.

In FIG. 7, outer tube 8 is shown as being received within cannula 28. Outer tube 8 is positioned toward the distal end of inner tube 4, having been used to advance a half-hitch through the cannula toward the remote sight.

Referring to FIGS. 8 through 11, a method of arthroscopic suture tying according to a preferred embodiment of the present invention is performed as follows:

1) A length of suture 30 is threaded through wire loop 16 of inserter 12, as shown in FIG. 8.
2) Referring to FIG. 9, suture 30 is threaded through the cannula of inner tube 4 using wire loop 16 to form post suture limb 32.
3) Referring again to FIG. 9, a first half-hitch loop is thrown around post suture 32, beyond the distal end of inner tube 4.
4) Inner tube 4 pushes the first loop distally along post suture 32, as shown in FIG. 10. With inner tube 4 holding the first half hitch in place, a second half-hitch loop is thrown around inner tube 4, between the distal end of inner tube 4 and the distal end of outer tube 8.
5) Referring to FIG. 11, outer tube 8 is advanced distally to push the second half hitch loop around the inner tube until it reaches the end of the inner tube, at which point the loop is tightened to form a knot.
6) Steps 1–6 are then repeated to form consecutive half hitches. The preferred technique is to alternate the direction of throw of each loop, thereby providing a more secure knot.

Referring to FIG. 12, a step of an alternative method of tying suture knots according to the present invention is shown. According to this alternative method, the first loop is thrown around inner tube 4, which is being used, for example, to hold tissue in place or to position the tissue during knot tying. The first loop is pushed distally along inner tube 4 using outer tube 8 and slipped over the end of inner tube 4, to be held in place as described above. The second loop then is thrown around inner tube 4. The alternative procedure is completed using steps 5–6 described above.

In an alternative embodiment, rather than inner tube 4 being received within outer tube 8, inner tube 4 can be replaced by another cannulated arthroscopic instrument, such as a suture anchor inserter as disclosed in U.S. Pat. No. 5,466,423, incorporated herein by reference. In this case, the suture anchor inserter, or other cannulated instrument, substitutes for the inner tube 4, and pushes the first half-hitch loop distally along the suture post, in the manner previously described. Outer tube 8, provided to fit snugly and slidably over the inserter, then pushes the second loop distally along the inserter to complete the knot.

Although the present invention has been described in relation to particular embodiments thereof, many other variations and modifications and other uses will become apparent to those skilled in the art. Accordingly, the present invention is to be limited not by the description above, but only by the appended claims.

What is claimed is:

1. An apparatus consisting essentially of:

an inner tube having a distal end for pushing and holding suture, a proximal end, a lumen, and an outer surface; and an outer tube disposed slidably over the inner tube, the outer tube having a distal end for pushing suture, a proximal end, and a lumen receiving the inner tube, wherein the distal end of the outer tube and the outer surface of the inner tube cooperate to prevent passage of suture between the inner tube and the outer tube when the outer tube is advanced toward the distal end of the inner tube to advance a loop of suture along the outer surface of the inner tube.

2. The apparatus of claim 1, further comprising a face on the distal end of the outer tube for contacting the suture.

3. The apparatus of claim 1, further comprising a handle disposed on the proximal end of the inner tube.

4. The apparatus of claim 3, wherein the handle on the inner tube comprises a cannulated disc.

5. The apparatus of claim 3, wherein the handle includes a suture retainer for holding a piece of suture.

6. The apparatus of claim 5, wherein the suture retainer comprises a tapered slot.

7. The apparatus of claim 1, further comprising a handle disposed on the proximal end of the outer tube.

8. The apparatus of claim 7, wherein the handle on the outer tube comprises a cannulated disk.

9. The apparatus of claim 1, further comprising means, disposed on the distal end of the inner tube, for holding tissue.

10. A kit for tying knots in suture comprising:

the apparatus of claim 1, and a suture passer, for threading the apparatus with suture, the suture passer being slidably disposable within the lumen of the inner tube.

11. The apparatus of claim 1, wherein the movement of the outer tube along the inner tube is limited in the proximal direction, and wherein the length of the outer tube is such that when the inner tube is disposed within a surgical cannula and the distal end of the inner tube extends beyond a distal end of the surgical cannula, a portion of the inner tube is exposed between a proximal end of the surgical cannula and the distal end of the outer tube.

12. The apparatus of claim 11, wherein the exposed portion of the inner tube is sufficient to receive a half hitch of suture to be formed around the inner tube.

13. A method of tying a knot using a knot pusher having a cannulated inner tube and an outer tube having a distal end slidably disposed over the inner tube, the method comprising the steps of:

introducing a length of suture material through the cannulated inner tube, a free end of the suture extending beyond the distal end of the inner tube;

forming a half hitch loop around the cannulated inner tube with the free end of the suture material;

contacting the half hitch loop with the distal end of the outer tube;

holding tissue with the distal end of the inner tube; and advancing the outer tube along the inner tube to push the half hitch distally along the inner tube with the distal end of the outer tube to form a knot.

14. The method of claim 13, further comprising the step of holding the knot with the distal end of the inner tube while forming another half hitch around the inner tube and advancing the another half hitch loop distally by sliding the outer tube along the inner tube.

15. The method of claim 14, wherein the step of forming the another half hitch is performed outside a body undergoing surgery.

16. The method of claim 13, wherein the step of forming the half hitch loop is performed outside a body undergoing surgery.

17. A method of tying a knot using a knot pusher having a cannulated inner tube having a distal end and an outer tube slidably disposed over the inner tube, the method comprising the steps of:

introducing a length of suture material through the cannulated inner tube, leaving a free end of the suture extending beyond the distal end of the inner tube;

forming a post with the free end of the suture;

forming a first half hitch loop around the post with the free end of the suture material;

contacting the first half hitch loop with the distal end of the inner tube; and advancing the inner tube along the post to push the first half hitch loop distally along the post using the distal end of the inner tube to form a knot.

18. The method of claim 17, further comprising the steps of:

holding the knot in place using the inner tube;

forming a second half hitch loop around the inner tube;

pushing the second half hitch loop distally along the inner tube using the distal end of the outer tube.

19. The method of claim 18, wherein the step of forming the second half hitch loop is performed outside a body undergoing surgery.

20. The method of claim 17, wherein the step of forming the first half hitch loop is performed outside a body undergoing surgery.

* * * * *